(12) United States Patent
Cattani

(10) Patent No.: US 6,423,124 B1
(45) Date of Patent: Jul. 23, 2002

(54) DEVICE FOR REGULATING A FLOW RATE IN AN AIR-LIQUID CENTRIFUGE SEPARATOR

(75) Inventor: Ennio Cattani, Parma (IT)

(73) Assignee: Cattani S.p.A., Parma (IT)

( * ) Notice: Subject to any disclaimer, the term of this patent is extended or adjusted under 35 U.S.C. 154(b) by 0 days.

(21) Appl. No.: 09/624,182

(22) Filed: Jul. 24, 2000

(30) Foreign Application Priority Data

Jul. 30, 1999 (IT) .......................................... MO99A0165

(51) Int. Cl.[7] .............................................. B01D 19/00
(52) U.S. Cl. .............................. 96/174; 96/156; 96/195; 95/19; 95/22; 95/248; 55/340
(58) Field of Search ...................... 96/156, 174, 193, 96/195, 397, 408, 157; 55/DIG. 14, 338, 340; 95/19, 22, 248, 254, 259, 261, 266; 494/1, 2, 5, 10, 56; 210/188; 222/72; 433/92

(56) References Cited

U.S. PATENT DOCUMENTS

| | | | | |
|---|---|---|---|---|
| 3,715,863 A | * | 2/1973 | Zanoni | 96/170 |
| 3,752,389 A | * | 8/1973 | Nilsson | 494/1 |
| 4,222,751 A | * | 9/1980 | Shunta | 96/172 |
| 4,475,897 A | * | 10/1984 | Bradtmöller | 494/10 |
| 5,190,515 A | * | 3/1993 | Eaton et al. | 96/174 |
| 5,513,704 A | * | 5/1996 | Sander | 55/344 |
| 5,884,809 A | * | 3/1999 | Wood et al. | 222/72 |
| 6,083,306 A | * | 7/2000 | Cattani | 96/157 |
| 6,179,163 B1 | * | 1/2001 | Bohr et al. | 222/72 |

FOREIGN PATENT DOCUMENTS

EP 0 023 036 1/1981

* cited by examiner

Primary Examiner—Duane Smith
Assistant Examiner—Jason M. Greene
(74) Attorney, Agent, or Firm—Browdy and Neimark P.L.L.C.

(57) ABSTRACT

The device for regulating a flow rate of an air-liquid centrifuge separator includes a gas outlet pipe, an outlet pipe for separated liquids and an inlet pipe through which a fluid to be separated enters the separator. The device includes a by-pass pipe, arranged between the liquid outlet pipe and the fluid inlet pipe, which removes liquid from the liquid outlet pipe and transfers it to the fluid inlet pipe when a pressure of the liquid in the liquid outlet pipe exceeds a predetermined level. The device is particularly useful in separators for dental aspiration plants.

12 Claims, 1 Drawing Sheet

DEVICE FOR REGULATING A FLOW RATE IN AN AIR-LIQUID CENTRIFUGE SEPARATOR

BACKGROUND OF THE INVENTION

Specifically, though not exclusively, the invention is usefully applied in the field of dental aspiration plants.

As is well known, dental aspiration plants enable fluids to be removed from the mouth of a patient during a dental operation. These fluids comprise a gaseous part, generally air, a liquid part, generally water, blood and other liquids which are used in the dental plant) and a solid part which is made up of particles, generally obturation material and other debris. The flow of the aspirated fluids, which contain various polluting substances, is usually discontinuous and can be quite substantial, such as, for example, when the plant is being washed and flushed out.

The separated liquids, before being discharged into the municipal sewers, have to be treated in order to remove the polluting substances. Whatever the nature of this treatment, a counter-pressure is generated in outlet which hinders the exit of the liquids from the plant. Other and many-varied factors (both constant and accidental) can cause a similar counterpressure.

In plants equipped with an air-liquid separator centrifuge, i.e. a separator in which the fluid to be separated enters and subsequently exits through different outlets, the air (or other gases) being aspirated by the separator, for example by a suction pump, and the liquid being sent on to subsequent treatments before being discharged into the sewers, it can happen that an excessive incoming fluid flow leads to difficulty in liquid discharge, possibly giving rise to a flooding in the separator, with liquid being sucked into the air outlet. This drawback is to be avoided, as it can lead to serious damage of the air suction pump.

As it is not possible to discharge any excess liquid directly into the sewers, various solutions have been offered to obviate this drawback.

A first of these solutions consists in halting plant operation (in practice this means shutting down the suction pump) when the liquid level or the pressure of liquid in the pipe goes over a certain level. This is a rather drastic solution which is not popular with users.

Another solution consists in providing a buffer tank which, when the level of the liquid or the pressure of the liquid in the pipe goes over a certain level, receives the excess liquid which is then sent on to subsequent treatments before being discharged into the sewers. This solution, though quite functional in other areas, leads to a complication in the construction of the plant as well as to an increase in its size.

SUMMARY OF THE INVENTION

The main aim of the present invention is to obviate the above-mentioned drawbacks in the prior art, by providing a device which simply and economically prevents separator flooding in any operating circumstances without shutting down aspiration plant operation.

An advantage of the device is that it can be easily applied on known-type plants.

A further advantage is that it provides a device which, in case of necessity, activates and deactivates automatically with no need for manual intervention on the part of the operator, nor any need for an external energy supply, such as electrical or pneumatic energy, or any other type.

These aims and advantages and more besides are all achieved by the invention as it is characterised in the claims that follow.

BRIEF DESCRIPTION OF THE DRAWINGS

Further characteristics and advantages of the present invention will better emerge from the detailed description that follows of a preferred but non-exclusive embodiment of the invention, illustrated purely by way of a non-limiting example in the accompanying figures of the drawings, in which.

DESCRIPTION OF THE PREFERRED EMBODIMENTS

Figure 1:
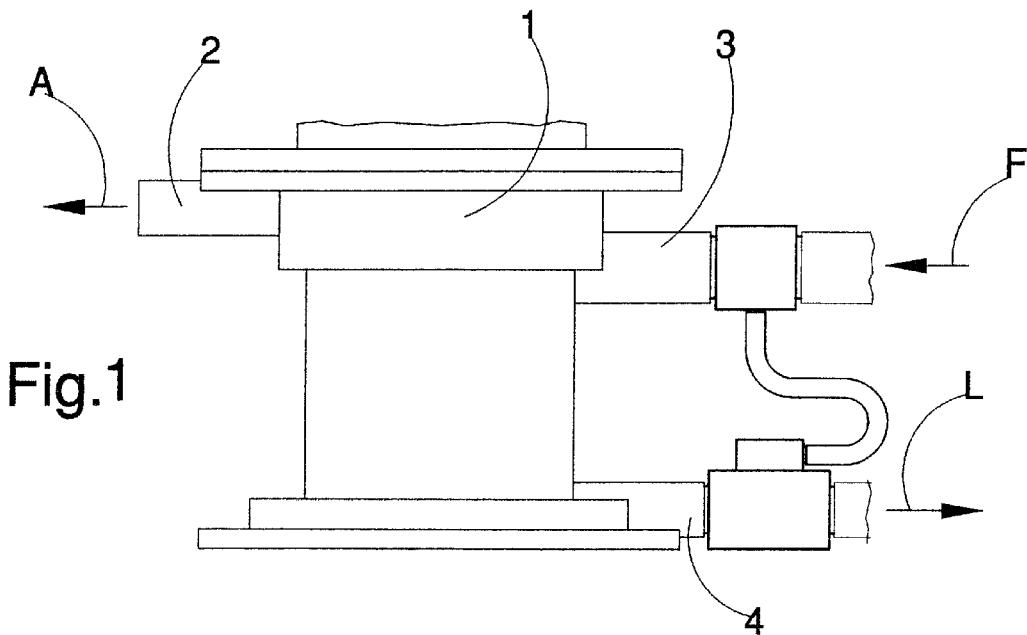
FIG. 1 is a diagram of an air-liquid separator centrifuge.
Figure 2:
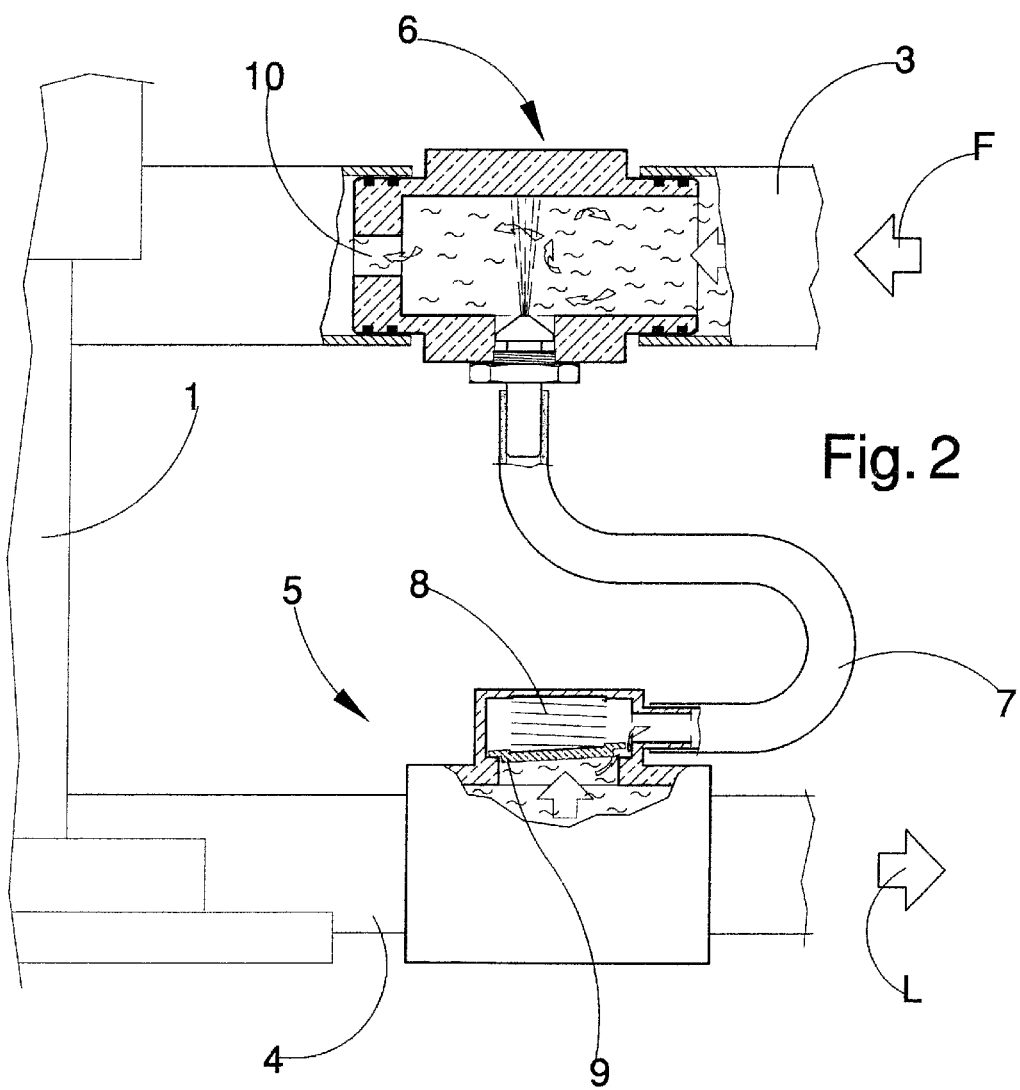
FIG. 2 is an enlarged-scale drawing of a detail of FIG. 1 relating to a possible embodiment of the device of the invention.

With reference to the figures of the drawings, 1 denotes in its entirety an air-liquid centrifuge separator, of known type, for separating a gaseous part of a fluid from a liquid part thereof. This type of separator centrifuge is commonly used, for example, in dental aspiration plants.

The inside of the separator 1 is kept in depression by means for aspirating, for example by a suction pump of known type and not represented in the figures. The suction pump aspirates the gaseous part of the fluid to be separated, and expels the gas through a gas outlet pipe 2, in the flow direction indicated by arrow A. The separator 1 further comprises a liquid outlet pipe 4, through which the separated liquids are sent in flow direction L to a liquid treatment device, for example a solid particle separator of known type and not represented in the figures. The fluid to be separated enters the separator 1 in flow direction F through a fluid inlet pipe 3; the fluid is sucked into the separator by effect of the depression inside the separator itself.

The device of the invention comprises a by-pass pipe 7 which is arranged between the liquid outlet pipe 4 and the fluid inlet pipe 3. When the liquid pressure in the liquid outlet pipe 4 exceeds a predetermined level, a part of the liquid is taken away from the liquid outlet pipe 4 and transferred to the fluid inlet pipe 3 through this by-pass pipe 7. The point at which the by-pass pipe 7 meets the fluid inlet pipe 3 is immediately upstream of the separator 1, while the connection with the liquid outlet pipe 4 is immediately downstream of the separator 1. This particular arrangement increases (as will become more evident herein below) the immediacy of the device response to an excess of liquid in the liquid outlet pipe 4.

The by-pass pipe 7 is connected to the liquid outlet pipe 4 through a pressure relief valve 5, which, in a preferred embodiment shown in the figures, is two-way and comprises an obturator 9, normally in the form of a membrane, which during normal operation is kept closed by an adjustable spring 8 (for example regulatable by a preload obtained using screws, not illustrated in the figures). The loading, or regulation, of the spring 8 decides on the pressure level at which the valve 5 opens and places the liquid outlet pipe 4 in communication with the by-pass pipe 7.

The fluid inlet pipe 3 comprises a sleeve 6 which exhibits a choke 10; the by-pass pipe 7 is connected to the fluid inlet pipe 3 at a point upstream of the choke 10 with respect to the separator 1; thus the ingress of the liquid from the by-pass pipe 7 into the sleeve 6 of the fluid inlet pipe 3 is countercurrent to the motion of the fluid internally of the fluid inlet pipe 3.

In the illustrated embodiment, the liquid enters in a perpendicular direction to that of the motion of the fluid internally of the fluid inlet pipe 3; this is solely for reasons of constructional simplicity and does not substantially affect the operation of the device in relation to a possible slightly more functional countercurrent ingress.

During normal operation, when there is no excess of liquid in the liquid outlet pipe 4, the valve 5 remains closed and the by-pass pipe 7 is not crossed by liquid or fluid, and the separator 1 functions normally.

When there is an excess of liquid, which might occur during a plant washing and flushing operation, when the amount of liquid aspirated with the fluid is greater, generally for quite brief periods, than the amount of fluid being discharged, the liquid level and pressure in the liquid outlet pipe 4 reach a predetermined level, which level is in any case lower than one which would cause separator 1 flooding, the valve 5 opens and the liquid is discharged through the by-pass pipe 7 into the fluid inlet pipe 3.

Inletting of liquid into the fluid inlet pipe 3 causes an increase in pressure upstream of the choke 10, with a consequent diminution in the volume of fluid aspirated. This means that there is effectively an automatic reduction in the volume of fluid aspirated, which tends to reduce the excess of liquid and brings the separator 1 back into normal operating condition parameters, without the plant having to be shut down, and even without the operator's noticing the change in operating mode, especially given the brevity of the excess fluid condition.

Once the liquid level in the liquid outlet pipe 4, and consequently the pressure therein, have returned to acceptable levels, the valve 5 automatically closes and the separator 1 returns to normal functioning.

It is worth noting that the positioning of the by-pass pipe 7 close to the separator 1 means that an increase in pressure is almost immediately detected, as is a reduction in the volume in the fluid inlet pipe 3.

The device of the invention realizes a device which perfectly solves the problem of preventing separator flooding, which has no need of maintenance, which can be applied to known-type plants, which enters into operation and deactivates with no need to shut the plant down. The device also has no need for manual intervention nor is any external supply required, but it processes the totality of the liquid sent to it, without the operator even noticing its entry into operation.

What is claimed is:

1. A device for regulating a flow rate in an air-liquid centrifuge separator, for application to a separator, comprising:
    a fluid inlet pipe at a first level, through which a fluid to be separated is sucked into the separator;
    a gas outlet pipe through which, aided by an aspirating device, gas is removed from a fluid to be separated;
    a liquid outlet pipe, through which a liquid separated from the gas is sent on to a further device for treatment of liquids, said liquid outlet pipe being located at a second level below said first level;
    wherein the device for regulating a flow rate comprises a by-pass pipe, extending upwardly between the liquid outlet pipe and the fluid inlet pipe, which by-pass pipe removes the liquid from the liquid outlet pipe and transfers the liquid upwardly to the fluid inlet pipe when a pressure of the liquid in the liquid outlet pipe exceeds a predetermined level.

2. The device of claim 1, wherein the by-pass pipe is arranged between the fluid inlet pipe and the liquid outlet pipe, and connects immediately upstream of the separator on the fluid inlet pipe and immediately downstream of the separator on the liquid outlet pipe.

3. The device of claim 1, wherein the by-pass pipe is connected to the liquid outlet pipe via a pressure relief valve.

4. The device of claim 3, wherein the pressure relief valve is two-way and comprises an obturator which is normally kept in a closed position by an adjustable spring.

5. The device of claim 1, wherein the fluid inlet pipe exhibits a sleeve having a choke; the by-pass pipe being connected to the fluid inlet pipe at a point which is upstream of the choke with respect to the separator.

6. The device of claim 5, wherein ingress of the liquid from the by-pass pipe into the sleeve is in a direction which is countercurrent to a motion direction of the fluid internally of the fluid inlet pipe.

7. A device for regulating a flow rate in an air-liquid centrifuge separator, for application to a separator the inside of which is kept in depression by an aspirating device which aspirates from the separator a gaseous part of a fluid to be separated, comprising:
    a fluid inlet pipe, through which the fluid to be separated is sucked into the separator by reduced pressure inside the separator;
    a gas outlet pipe, through which the aspirating device removes the gas from the fluid to be separated and expels the gas from an upper part of the separator;
    a liquid outlet pipe, through which a liquid separated from the gas is removed from the bottom of the separator and is sent on to a further device for treatment of liquids;
    a by-pass pipe, arranged between the liquid outlet pipe and the fluid inlet pipe, which does not pass therethroughy liquid or fluid when there is no excess of liquid in the separator, and which removes the liquid from the liquid outlet pipe and transfers the liquid to the fluid inlet pipe when the liquid level exceeds a predetermined level.

8. The device of claim 7, wherein the by-pass pipe is arranged between the fluid inlet pipe and the liquid outlet pipe, and connects immediately upstream of the separator on the fluid inlet pipe and immediately downstream of the separator on the liquid outlet pipe.

9. The device of claim 7, wherein the by-pass pipe is connected to the liquid outlet pipe via a pressure relief valve.

10. The device of claim 9, wherein the pressure relief valve is two-way and comprises an obturator which is normally kept in a closed position by an adjustable spring.

11. The device of claim 7, wherein the fluid inlet pipe exhibits a sleeve having a choke; the by-pass pipe being connected to the fluid inlet pipe at a point which is upstream of the choke with respect to the separator.

12. The device of claim 11, wherein ingress of the liquid from the by-pass pipe into the sleeve is in a direction which is countercurrent to a motion direction of the fluid internally of the fluid inlet pipe.

* * * * *